United States Patent
Kwok et al.

(10) Patent No.: US 10,434,193 B2
(45) Date of Patent: Oct. 8, 2019

(54) COMPOSITION FOR USE IN MEDICAL IMAGING AND A METHOD FOR PREPARING THEREOF

(71) Applicant: Jacobson Research Laboratory Limited, Kowloon (HK)

(72) Inventors: Connie Sau-Kuen Kwok, Satin (HK); Kwok Kin Cheng, Shatin (HK)

(73) Assignee: Jacobson Research Laboratory Limited, Kowloon (HK)

( * ) Notice: Subject to any disclaimer, the term of this patent is extended or adjusted under 35 U.S.C. 154(b) by 0 days.

(21) Appl. No.: 15/831,661

(22) Filed: Dec. 5, 2017

(65) Prior Publication Data

US 2018/0236108 A1    Aug. 23, 2018

Related U.S. Application Data

(63) Continuation-in-part of application No. 15/436,922, filed on Feb. 20, 2017.

(51) Int. Cl.
*A61K 49/18* (2006.01)

(52) U.S. Cl.
CPC ........ *A61K 49/1854* (2013.01); *A61K 49/186* (2013.01); *A61K 49/1881* (2013.01)

(58) Field of Classification Search
None
See application file for complete search history.

(56) References Cited

PUBLICATIONS

Warringer, S., et al., "Metal complexes of curcumin—synthetic strategies, structures and medicinal applications", Chem. Soc. Rev., 2015, pp. 4986-5002 (Year: 2015).*
Pourreza, N., et al., "Colorimetric sensing of oxalate based on its inhibitory effect on thereaction of Fe (III) with curcumin nanoparticles", Spect. Acta A., Nov. 2017, pp. 251-256 (Year: 2017).*
Mohammed, F., et al., "A comparative study of the spectral,fluorometric properties andphotostability of natural curcumin, iron- and boron-complexed curcumin" Spect. Acta A, May 2017, pp. 439-450 (Year: 2017).*
Yang, J., et al., "Oxalate-curcumin-based probe for micro- and macroimaging of reactive oxygen species in Alzheimer's disease", PNAS, Nov. 2017, pp. 12384-12389 (Year: 2017).*

* cited by examiner

*Primary Examiner* — Johann R Richter
*Assistant Examiner* — Lance W Rider

(57) ABSTRACT

The present invention relates to a composition for use as a contrast agent in medical imaging. The composition comprises a metal ion containing compound comprises at least one metal ion adapted to bind with one or more metal ion chelating agents; wherein said one or more metal ion chelating agents comprise at least one first chelating agent adapted to target a region of interest being imaged, and at least one second chelating agent having at least one functional group adapted to dissociate in an aqueous medium to thereby allow or enhance contrast of the region of interest under the medical imaging. The present invention further relates to a diagnostic agent for use in amyloid (Aβ) protein detection under magnetic resonance imaging (MRI) comprising the above described composition; and a method of preparing thereof.

24 Claims, 17 Drawing Sheets

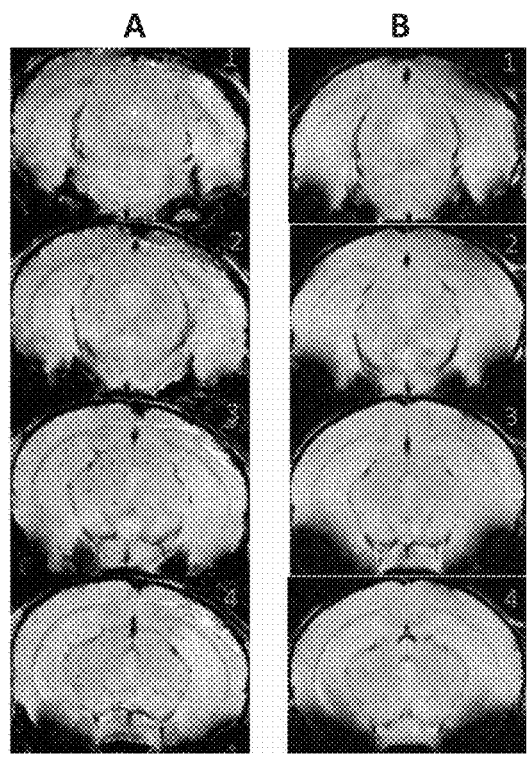
FIG. 14 (1-4)
(Con't)

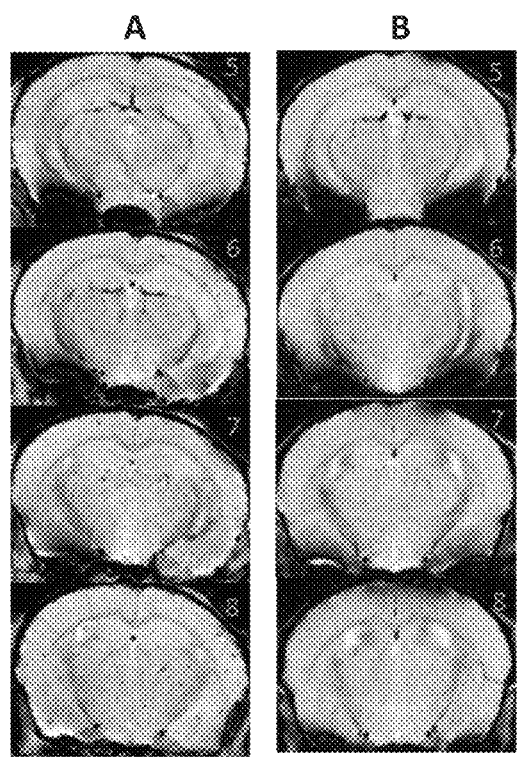
FIG. 14 (5-8)
(con't)

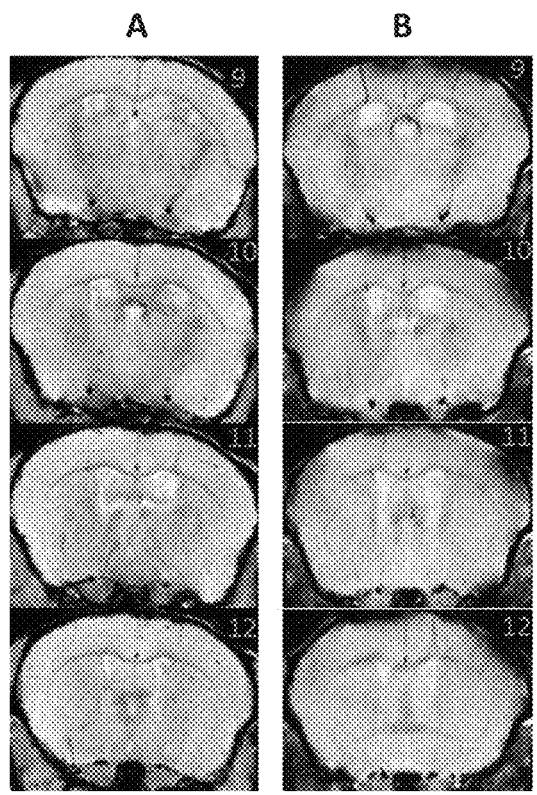
FIG. 14 (9-12)
(con't)

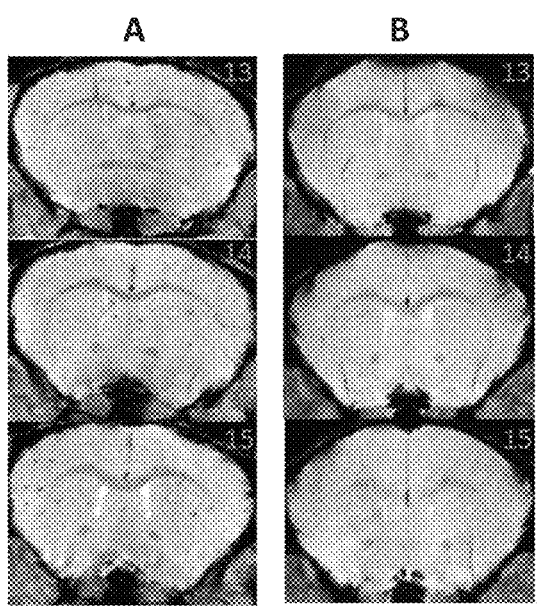
FIG. 14 (13-15)

COMPOSITION FOR USE IN MEDICAL IMAGING AND A METHOD FOR PREPARING THEREOF

FIELD OF THE INVENTION

The invention relates to a composition for use in the field of medical imaging, and particularly, but not exclusively, to a composition for use in detecting or diagnosing a protein-related, neurodegenerative disease in a subject under Magnetic Resonance Imaging (MRI), such as, but not limited to, Alzheimer's disease (AD).

BACKGROUND OF THE INVENTION

Alzheimer's disease (AD) is a progressive neurodegenerative disorder which presents the highest prevalence rate among a number of dementing diseases. The disease may initially affect cognitive abilities such as memory loss and other intellectual abilities, and in the advanced stage, patients may suffer from the loss of motor functions and may require assistance from others in performing basic, daily life activities. Recent studies have revealed that, among the 40 million people worldwide who suffer from dementia, around 60% to 80% of these cases have been classified as Alzheimer's disease. Although the risk factor of Alzheimer's disease is known to increase with age, about 5% of the total AD patients are diagnosed with early onset, i.e. with symptoms first appearing before 65 years of age. As life expectancy continuously rises, it is predicted that the prevalence of AD will drastically increase in the near future.

Despite advancements in medical technology, Alzheimer's disease (AD) is still considered incurable, with the drugs currently available only providing partial relief of the symptoms, but which do not slow down or reverse the degeneration of brain functions caused by the disease. Although the causes of AD have not been clearly identified, one commonly known hypothesis is that the disease may be related to or caused by the abnormal aggregation of beta amyloid (Aβ) proteins in brain tissues of the patient. The ability to identify or detect the presence of these beta amyloid (Aβ) aggregates at an early stage is therefore of significant importance to the diagnosis and treatment of the disease.

Nevertheless, available methods for diagnosing Alzheimer's disease are found to be inadequate and inefficient. For example, a radioactive positron emission tomography (PET) imaging reagent that binds to amyloid plaques was recently approved for clinical use. However, it is known to suffer from the short-comings of high cost, limited availability, toxic radioactivity and particularly, low spatial resolution such that individual plaques are difficult if not impossible to be clearly visualized. Another approach which uses Magnetic Resonance Imaging (MRI) to diagnose Alzheimer's disease involves the use of potentially toxic reagents which limit the maximum safe dosage administrable to a patient and accordingly, limits the sensitivity and accuracy of the method. In this connection, various contrast agents have been developed with an aim to improve or enhance contrast of the detected regions of interest in the MRI images and thus sensitivity of the MRI. For example, chelates of gadolinium have been used as intravenous contrast agents. However, gadolinium is known to exhibit toxicity at high concentration which affects functions of kidney and may even cause renal failure. Recent studies also revealed that, after the use of gadolinium contrast agents during an MRI study, a small amount of at least some forms of gadolinium is found to retain in certain tissues, which may pose a potential risk to the patient.

It is further reported by K K Cheng et al. in *Biomaterials* 44 (2015) 155-172 published on 12 Jan. 2015 and in US Patent Application Publication No. US 2017/0196998 A1 that iron oxide particles with surfaces coated with curcumin, a naturally occurring compound extracted from turmeric, the root of the *Curcuma longa* plant, demonstrated ability to bind to beta amyloid (Aβ) plaques in brain tissues of mice and are detectable under MRI. However, the technique still shows insufficiencies in terms of signal sensitivity and spatial resolution in practice for Alzheimer's disease detection, as well as the process in preparing the particles.

OBJECTS OF THE INVENTION

An object of the present invention is to provide an agent for use in medical imaging such as, but not limited to, MRI for identifying one or more neurodegenerative diseases or conditions related protein molecules.

Another object of the present invention is to provide an agent for use in MRI for detecting or diagnosing one or more neurodegenerative diseases in a subject such as, but not limited to, Alzheimer's disease.

A further object of the present invention is to provide a contrast agent which allows or enhances contrast of the detected region of interest of a subject under the MRI.

A yet further object of the present invention is to mitigate or obviate to some degree one or more problems associated with known imaging techniques for brain or brain tissues, or at least to provide a useful alternative.

The above objects are met by the combination of features of the main claims; the sub-claims disclose further advantageous embodiments of the invention.

One skilled in the art will derive from the following description other objects of the invention. Therefore, the foregoing statements of object are not exhaustive and serve merely to illustrate some of the many objects of the present invention.

SUMMARY OF THE INVENTION

In general, the invention provides an agent for use in medical imaging such as, but not limited to, Magnetic Resonance Imaging (MRI) for identifying, showing, determining, detecting or targeting, and more specifically, allowing or enhancing visibility or contrast of the identified, detected or targeted region of interest of a subject under the imaging technique. The region of interest may comprise one or more proteins or protein molecules relating to one or more neurodegenerative diseases or conditions such as, but not limited to, Alzheimer's disease (AD). Particularly, the present invention provides a composition comprising a metal ion-metal ion chelating agent complex identifiable under the MRI, and preferably, with an improved or enhanced contrast. In one embodiment, the composition comprises a complex formed of iron metal ion, curcumin and oxalate, and more preferably, a complex formed of iron metal ion, curcumin and oxalate prepared in the form of nanoparticles. Specifically, the curcumin ligand of the complex allows binding of the complex with one or more of an aggregate, plaque, tissue, deposit, fibril, oligomer and/or molecule of any forms of beta amyloid (Aβ) proteins. The oxalate ligand of the complex is capable of dissociating slowly or in a controlled manner in an aqueous environment, for example, in the blood stream or body fluid of the subject being adminstered with the composition. In particular, dissociation of the oxalate ligand enables the coordinate structure of the complex to "open up" thereby allowing an efficient exchange of water from the aqueous surrounding with the central metal ion, which significantly improves or enhances contrast signal of the examined region of interest under the MRI.

In contrast to the prior technologies which allow tagging or labelling of beta amyloid (Aβ) plaques in brain tissues to reveal the affected regions at low sensitivity and spatial resolution under MRI, the present invention is advantageous in providing metal ion-curcumin-oxalate complex nanoparticles of sufficiently small size which enable binding of the nanoparticles not only to the relatively large targets of beta amyloid (Aβ) plaques, but also beta amyloid (Aβ) fibrils or even oligomers, which are typically too small to be effectively traceable or taggable in traditional practices. The present invention therefore demonstrates a significant improvement to the current technology which allows the screening and/or diagnostic of AD at a much earlier stage. In addition, the present invention offers an improved or enhanced contrast of the targeted beta amyloid (Aβ) proteins when viewed under the MRI, which assists in increasing diagnostic accuracy even when used at a relative low dosage. The present invention further provides a relatively simple and inexpensive method in preparing the complex nanoparticles, with high reproducibility and stability achievable.

In a first main aspect, the invention provides a composition for use as a contrast agent in medical imaging. The composition comprises a metal ion containing compound comprises at least one metal ion adapted to bind with one or more metal ion chelating agents; wherein said one or more metal ion chelating agents comprise at least one first chelating agent adapted to target a region of interest being imaged, and at least one second chelating agent having at least one functional group adapted to dissociate in an aqueous medium to thereby allow or enhance contrast of the region of interest under the medical imaging.

In a second main aspect, the invention provides a diagnostic agent for use in amyloid (Aβ) protein detection under magnetic resonance imaging (MRI). The diagnostic agent comprises the composition according to the first main aspect.

In a third main aspect, the invention provides a method of preparing a particle composition for use in medical imaging. The method comprises the steps of providing a metal ion-chelating agent complex in an organic solution to form an organic phase; introducing an amphiphilic copolymer to the organic phase to form an organic mixture; and mixing an aqueous phase with the organic mixture thereby forming core-shell particles each having a metal ion-chelating agent complex comprising core and an amphiphilic copolymer comprising shell.

The summary of the invention does not necessarily disclose all the features essential for defining the invention; the invention may reside in a sub-combination of the disclosed features.

BRIEF DESCRIPTION OF THE DRAWINGS

The foregoing and further features of the present invention will be apparent from the following description of preferred embodiments which are provided by way of example only in connection with the accompanying figure, of which:

FIG. 14 are serial MRI images showing whole brain scans on an experimental, AD diseased mouse (see column A) and a control, healthy mouse (see column B) from a rear position (#1) to a frontal position (#15) of their brains, with both of the scanned mice being injected with the stabilized iron ion-curcumin complex core-shell nanoparticles of FIG. 4.

DESCRIPTION OF PREFERRED EMBODIMENTS

Figure 1:
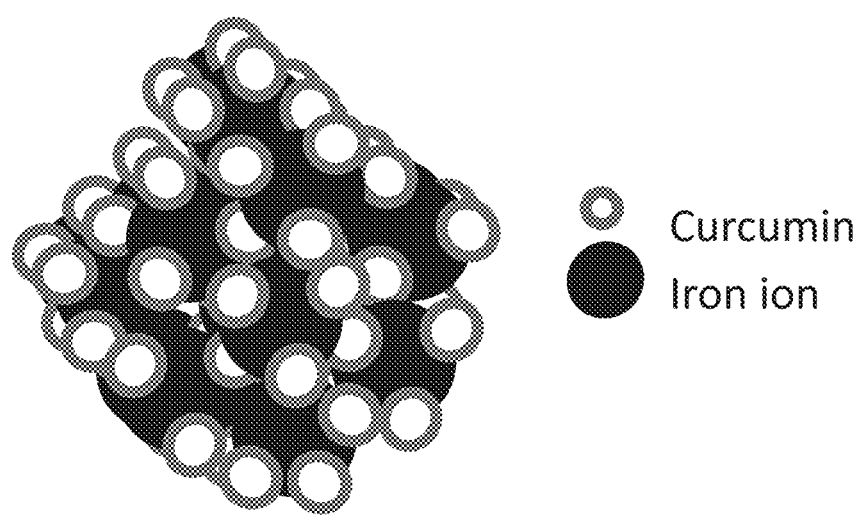
FIG. 1 is a schematic diagram showing an embodiment of the iron ion-curcumin complex in accordance with the present invention.

The following description is of preferred embodiments by way of example only and without limitation to the combination of features necessary for carrying the invention into effect.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

In the context of the present description, the expression "metal ion chelating agent" or "chelating agent" generally relates to a compound, either naturally occurred or synthetic, capable of binding with a metal or a metal ion to form a complex or a chelate complex. The terms "complex", "complexing" and/or "complexation" generally relate to a physical attraction or chemical reaction such as, but not limited to, ionic bonding or hydrogen bonding between one or more ligands with one or more metal ions. The expression "metal ion-chelating agent complex" or "metal ion-metal ion chelating agent complex" generally relates to a structure formed by complexation or chelation between one or more metals, metal ions, metal atoms or a mixture thereof and one or more chelating agents or metal ion chelating agents. The expression "iron metal ion-curcumin complex", "iron ion-curcumin complex" or "iron-curcumin complex" (represented by the formula $FeCur_3$); or "iron metal ion-curcumin-oxalate complex", "iron ion-curcumin-oxalate complex" or "iron-curcumin-oxalate complex" (represented by the formula $FeCurOx_2$ or $FeCur_2Ox$) generally relates to a complex formed with one or more curcumin molecules including curcumins, compounds of curcumin, curcumin derivatives and/or a mixture thereof, one or more iron metals, iron metal ions, iron metal atoms or a mixture thereof, and optionally, one or more oxalates, oxalates derivatives, salts thereof or a mixture thereof.

Curcumin is a naturally occurring botanical extract and has been studied for its potential applications in the treatment of a number of diseases and conditions in human and animal subjects due to their anti-inflammatory, anti-oxidizing, anti-cancer and metal ion-chelating properties. Particularly, curcumin has been shown to be capable of binding with beta amyloid (Aβ) aggregates and thus, has demonstrated potential to be used as indicators for Alzheimer's disease based on a well-accepted hypothesis that the disease is likely to be related to or caused by the abnormal aggregations of beta amyloid (Aβ) proteins in brain tissues.

Oxalate, also known as ethanedioate, is the conjugate base of oxalic acid. Various oxalates, particularly in the form of metallic oxalates, can be found as organic minerals or crystals naturally occurred in the nature including soils, rocks and among a variety of living organisms including plants and animals. Oxalate is known to be a potent chelating agent which usually binds as a bidentate ligand with a metal or metal ion to form a metal complex in coordinate structure. Recent studies have revealed that oxalates are potentially applicable in the pharmaceutical industry as drug delivery systems, especially due to their biodegradable and biocompatible characteristics in general.

The present invention relates to a composition for use as a contrast agent in medical imaging such as, but not limited to, Magnetic Resonance Imaging (MRI) for identifying, showing, determining, targeting or more specifically, allowing or enhancing visibility or contrast of the identified, detected or targeted region of interest of a subject under the imaging technique. The region of interest may comprise one or more proteins or protein molecules, and particularly, proteins or protein molecules relating to one or more neurodegenerative diseases or conditions such as, but not limited to, Alzheimer's disease (AD). The composition can be potentially applied as, for example, a contrast agent, a diagnostic agent, an indicator and/or a probe during the medical imaging process of the subject. Particularly, the composition can be used to allow, enhance and/or improve visibility and/or contrast of structures and/or regions of interests as shown by the medical images generated, and/or to detect, determine and/or reveal certain conditions and/or functions of the structures and/or regions being examined under the medical imaging process.

Specifically, the particle composition can be used with, for example, MRI, for visualizing, enhancing the received signal of, and/or determining or identifying the presence of one or more proteins or aggregates of the proteins, and preferably, one or more proteins or aggregates of the proteins relating to one or more neurodegenerative diseases or conditions. In one embodiment, the proteins may comprise, but are not limited to beta amyloid (Aβ) proteins. The particle composition may further be applicable in diagnosing one or more protein-related neurodegenerative diseases or conditions such as, but not limited to, Alzheimer's disease, Parkinson's disease, Lewy body disease, and/or other dementing conditions, etc.

Although the technique of medical imaging described and exemplified herein relates mainly to Magnetic Resonance Imaging (MRI), it will be appreciated that the present invention should not be restricted to the application of MRI, but any other means of medical imaging, techniques, instruments and tomographic scanners or the like, whether or not they are primarily designed to generate an image as such, shall also be encompassed, as long as they are considered suitable and applicable for the present invention without departing from the inventive concept.

Figure 2:
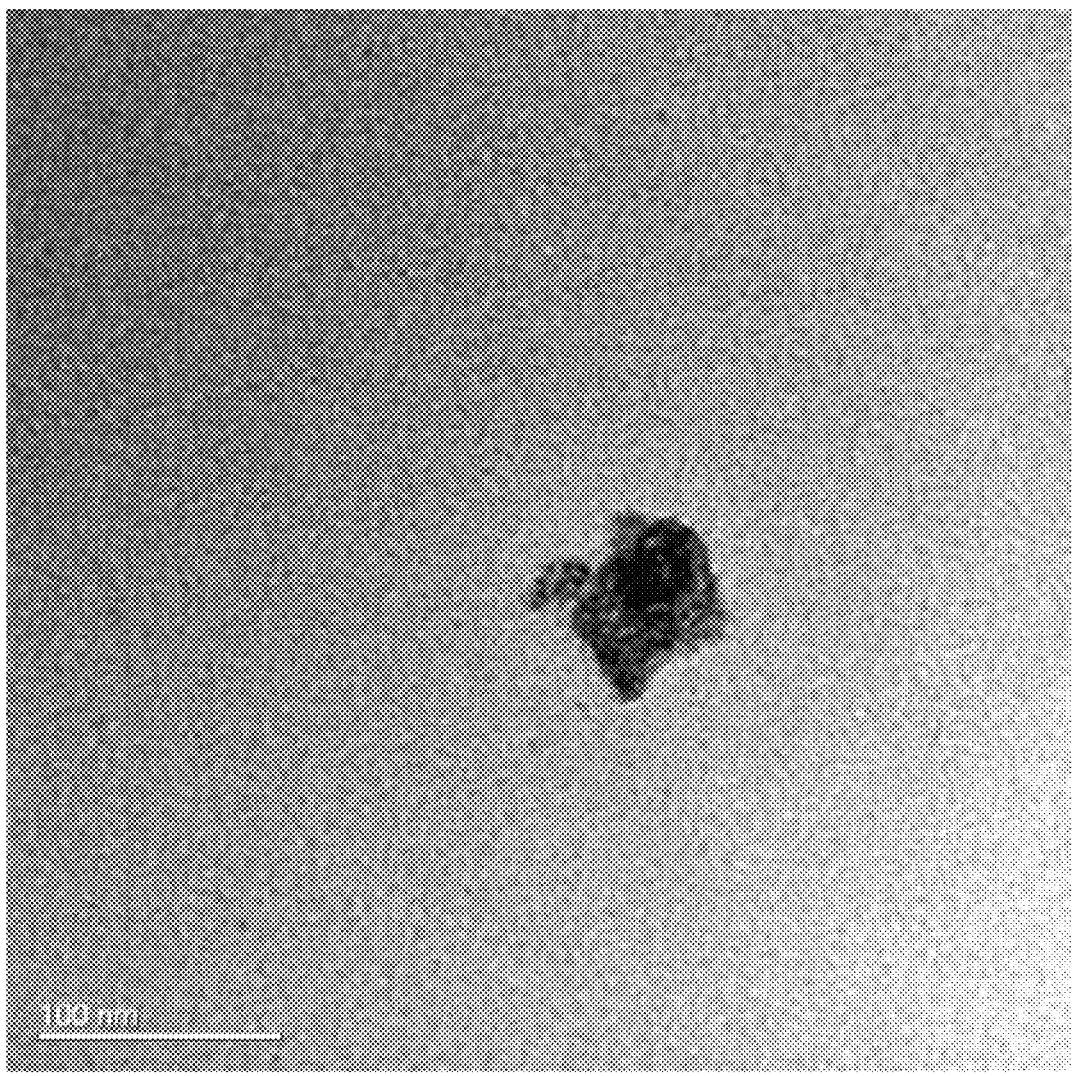
FIG. 2 is a transmission electron microscopy (TEM) showing the embodied complex of FIG. 1.

A number of embodiments of the present invention are herein described as follows:

Referring to FIGS. 1-2, shown is an embodiment of the particle composition in accordance with the present invention. As illustrated in the schematic diagram of FIG. 1, the particle composition comprise a metal ion containing compound, preferably in the form of particles or particulates, having at least one metal ion, such as but not limited to, an iron ion, with the iron metal ion being complexed with one or more metal ion chelating agents, such as but not limited to, a curcuminoid or curcuminoid containing compound and/or derivative thereof, and preferably, curcumin. In this embodiment, the complexation between the iron metal ion and the curcumin are found to be attributed to the natural affinity between curcumin with a number of metal ions, such as iron, copper and zinc, etc. in their metallic or ionic forms. It is also this natural affinity which allows the formed iron ion-curcumin complex in combining with one another to become a larger cluster or aggregate thereby forming particles or particulates. For example, in one specific embodiment as described herein, the iron ions or iron atoms are allowed to bind with the curcumin ligands to thereby enable the iron-curcumin complex or iron ion-curcumin complex to grow in size thus forming the iron-curcumin complex particles. Throughout the iron-curcumin complex particle, the curcumin and the iron metal ion are preferably randomly located as a cluster due to the ionic attractions therebetween, for example, as shown in FIG. 1, with the bound curcumin being randomly deposited both inside and outside the complex particles, i.e. both inside the particles and on the surfaces of the particles. This is in contrast to some prior art technologies, and particularly, those taught by Cheng in *Biomaterials*, which require coating of curcumin onto surfaces of the iron oxide seed particles via specific conjugating or coating steps to form substantially a single or multiple curcumin layers on the surfaces of the iron oxide seed particles.

As described earlier, curcumin is known to be able to bind to various amyloid proteins including beta amyloid, although the mechanism causing the binding is not yet clearly understood. In the present invention, the ability for curcumin to bind with both the iron ions and also, beta amyloid at different regions of the curcumin ligand molecule allows the beta amyloid to become visible or visible with enhanced contrast or resolution under the MRI due to the characteristic of the iron-comprising complexes as being magnetisable under the magnetic field of the MRI. Particularly, it is observed that the various complexes or complex particles as embodied in the present invention demonstrate single-domain magnetism, which is known to provide an enhanced magnetic signal when compared with other forms of magnetization such as super paramagnetism.

In particular, the very small size of the resulting nanoparticles as achieved by the present invention, for example, with an average diameter equal to or smaller than about 100 nm, and preferably, equal to or smaller than about 50 nm, enables binding of the particles to fibrils or oligomers of the beta amyloid protein. This facilities diagnosis of the relevant beta amyloid related diseases or conditions, such as Alzheimer's disease, at their early stage.

In one embodiment, the metal ion containing compound of the particle composition can be magnetisable under at least one of an electromagnetic wave, an electric field and a magnetic field; preferably, under a magnetic field with a strength ranged from about 1 Tesla (T) to about 9 T; and more preferably, about 3 T for an MRI operation on a human subject. The metal ion may comprise one or more of a ferromagnetic metal ion or metal ion alloy, such as but not limited to, iron ion. Alternatively, the metal ion may also comprise one or more transition metals or metal ions, such as but not limited to, iron, zinc and/or copper etc. in their metallic or ionic forms, as long as they are capable of complexing with one or more metal ion-chelating agents such as but not limited to, curcumin and/or oxalate, as exemplified in the embodiments later described, for example. In one embodiment, the chelating agents may comprise one or more curcumin molecules such as but not limited to, curcumins, curcuminoids, flavonoids, resveratrols, compounds or derivatives thereof and/or mixture thereof. In one further embodiment, the chelating agent may comprise one or more curcumin molecules and/or oxalate molecules such as but not limited to, oxalates, oxalate derivatives, salts thereof or a mixture thereof. Alternatively, the chelating agents may also be selected from a group consisting of bidentate chelating ligands such as ethylenediamine, 2,2'-bipyridine, 1,10-phenanthroline, acetylacetonate, 1,2-bis(diphenylphosphino)ethane, and 1,1-bis(diphenylphosphino)methane; tridentate chelating ligands such as iminodiacetic acid, trispyrazolylborate, 2,2':6',2''-terpyridine, and triazacyclononane; hexadentate chelating ligands such as ethylenediaminetetraacetic acid; pentafentate chelating ligands such as ethylenediaminetriacetate; and octodentate chelating ligands such as ethyleneglycolbis(oxyethylenenitrilo)tetraacetate.

The metal ion chelating agent may comprise one or more synthetic, naturally occurring, and/or naturally derived compounds. In one embodiment, the metal ion chelating agent may comprise synthetic molecules or compounds which are designed to mimic one or more of a naturally occurring and a naturally derived compounds. The metal ion chelating agent are capable of binding with one or more metal atoms and/or ions such as, but not limited to, one or more of iron, copper, and/or zinc in their metallic or ionic forms. Alternatively, the metal ion chelating agent can be a natural or synthetic compound comprising one or more metal binding moieties or functional groups such as, but not limited to, phenol, keto and/or hydroxyl groups, and preferably, be a polyphenol bearing compound, with the binding moieties or functional groups being capable of binding or interacting with beta amyloid (Aβ) proteins.

Preferably, the metal ion containing compound comprises an iron metal ion-curcumin complex, i.e. a result of an ionic complexation process between iron atoms and/or ions with curcumin, to form one or more particles or particulates; and more preferably, each with an average size of equal to or smaller than about 100 nm in diameter, and more preferably, equal to or smaller than about 50 nm. FIG. 2 shown a TEM of an iron-curcumin complex particle as embodied in the present invention having a diameter of about 65 nm.

Figure 3:
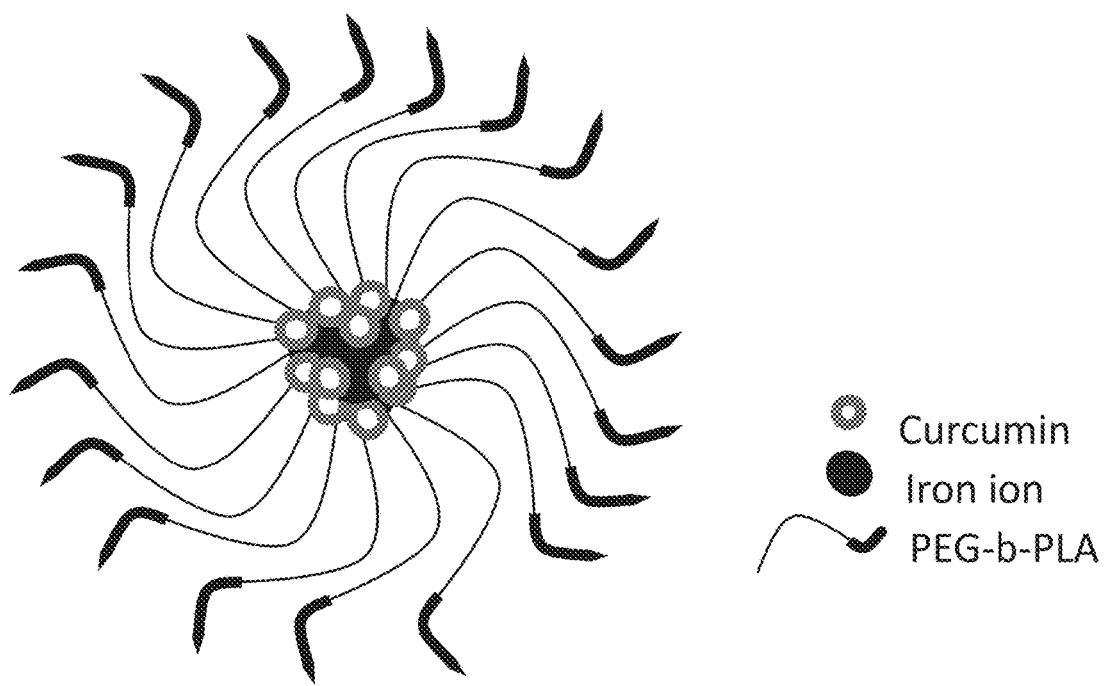
FIG. 3 is a schematic diagram showing an embodiment of a core-shell nanoparticle having an iron ion-curcumin complex core and an amphiphilic PEG-b-PLA copolymer shell in accordance with the present invention.

In one embodiment, the iron-curcumin complex particles are preferably surrounded by amphiphilic copolymers thereby forming particles with core-shell structures, i.e. each comprising an iron-curcumin complex core surrounded by an amphiphilic copolymers comprising shell, as shown in FIG. 3. Preferably, the amphiphilic copolymers each comprises at least one hydrophilic block and at least one hydrophobic block, with the hydrophilic block being preferred to be shorter than the hydrophobic block. More preferably, the amphiphilic copolymers are biocompatible. For example, the amphiphilic copolymers can be selected from a group consisting of polyethylene glycol (PEG)-b-polylactic acid (PLA), polyethylene glycol (PEG)-b-polycaprolactone (PCL), polyethylene glycol (PEG)-b-polylactic-co-glycolic acid (PLGA), pethoxypolyethylene glycol (MePEG)-b-polylactic acid (PLA), pethoxypolyethylene glycol (MePEG)-b-polycaprolactone (PCL), pethoxypolyethylene glycol (MePEG)-b-polylactic-co-glycolic acid (PLGA), polyethylene oxide (PEO)-b-polybutadiene (PBD), and a mixture thereof. More preferably, the amphiphilic copolymer is a diblock copolymer with a shorter hydrophilic PEG block and a longer hydrophobic PLA block such as, for example, a PEG(2k)-b-PLA(10k) copolymer, with the hydrophobic PLA block being arranged to adjacent the iron-curcumin complex core, and the hydrophilic PGA block being arranged to distal and extended away from the iron-curcumin complex core, as illustrated in FIG. 3.

Figure 4:
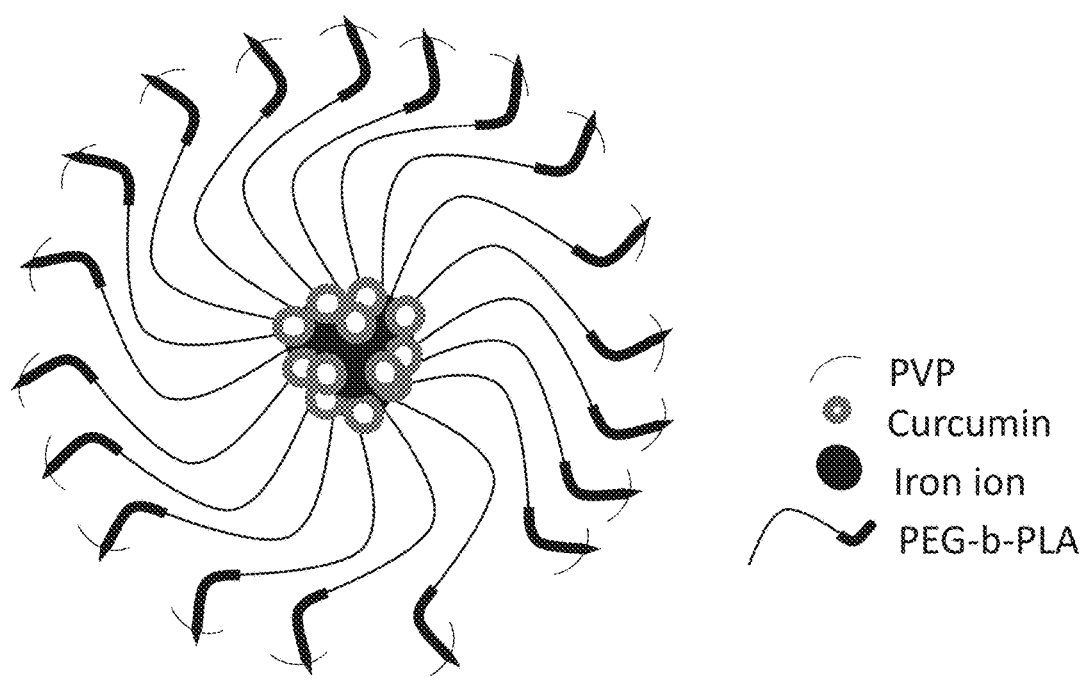
FIG. 4 is a schematic diagram showing the core-shell nanoparticle of FIG. 3 stabilized by PVP in accordance with the present invention.

In one further embodiment, the core-shell nanoparticles may further be stabilized by using a stabilizing agent such as a surfactant. The surfactant may be selected from a group consisting of polyvinyl pyrrolidone (PVP), polyvinyl alcohol (PVA), polyethylene glycols (PEG), hydroxypropyl methylcellulose (HPMC), poloxamers, polylactic-co-glycolic acid (PLGA), poly caprolactone (PCL), polylactic acid (PLA), poly(butyl)cyanoacrylate (PBCA), chitosan and a mixture thereof. The stabilization of the core-shell structure can be achieved by using PVP as illustrated in FIG. 4, for example.

Despite the above described examples of amphiphilic copolymers and surfactants, one skilled in the art will appreciate that the present invention should not be restricted to the specific examples provided, but any other compounds, reagents or the like shall also be encompassed as long as they are considered suitable and applicable for the present invention without departing from the inventive concept.

Figure 5:
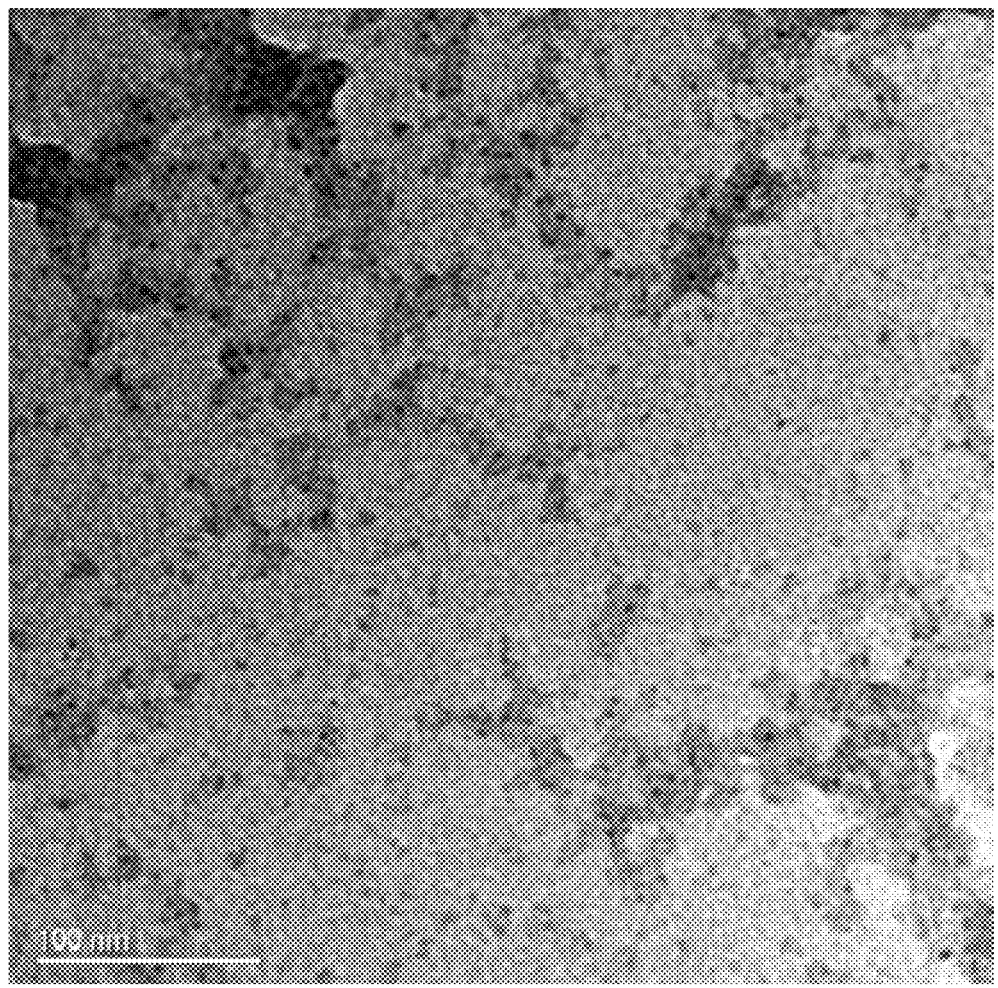
FIG. 5 is a TEM showing an embodiment of the stabilized core-shell nanoparticles of FIG. 4.
Figure 6:
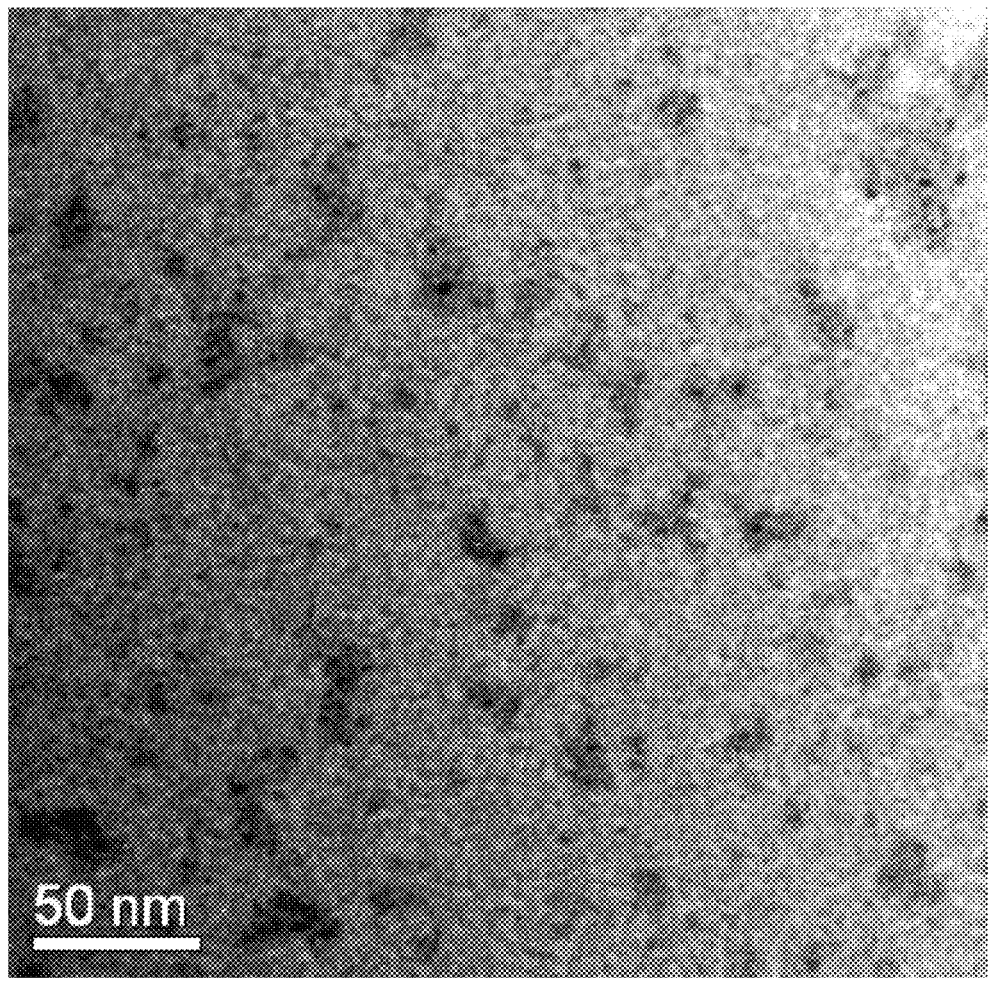
FIG. 6 is another TEM showing a magnified view of the stabilized core-shell nanoparticles of FIG. 4.

Preferably, the stabilized core-shell particles are of an average size equal to or smaller than about 50 nm in diameter. For example, the TEM of FIGS. 5 and 6 shown the core-shell particles in accordance with an embodiment of the present invention with an average diameter of about 20-30 nm, with the core of each of the core-shell structure equals to or smaller than about 10 nm. The sufficiently small size of the iron-curcumin complex core of the core-shell nanoparticles enable binding of the nanoparticles not only to the relatively large targets of the beta amyloid (Aβ) plaques, but also beta amyloid (Aβ) fibrils and/or oligomers, which are typically too small to be effectively traceable and/or taggable in practice.

In another aspect, the present invention also relates to a method of preparing one or more of the above described embodiments of the particle composition. The method may comprise the steps of, for example, providing a metal ion containing compound comprises at least one metal ion such as, but not limited to, iron metal ion complexed with one or more metal ion chelating agents such as, but not limited to, curcumin thereby forming an iron-curcumin complex. Preferably, the complex is prepared by having iron and curcumin in a ratio ranging from about 1:2 to about 1:5, and more preferably, iron and curcumin in about 1:3 mole ratio, for example.

The iron-curcumin complex can be formed by various complexing mechanisms including, for example, complexation due to ionic attraction between the metal ion chelating agent and one or more metal ions. Preferably, the iron-curcumin complex is prepared in the form of particles with an average size equal to or smaller than about 100 nm in diameter, or more preferably, equal to or smaller than about 50 nm in diameter.

The method may further comprise dissolving the iron-curcumin complex in an organic solvent to form an organic phase. The organic solvent can be any solvents capable of substantially or fully dissolving the iron-curcumin complex, which can be, for example, dimethyl formamide (DMF), dimethyl sulfoxide (DMSO), acetone, ethanol or a mixture thereof. Following the preparation of the iron-curcumin complex containing organic phase, the next step is to introduce one or more amphiphilic copolymers, as described earlier, to the iron-curcumin complex containing organic phase. In one embodiment, this can be done by introducing or dissolving the copolymers directly to the organic phase to form an organic mixture. Alternatively, the copolymers can be priorly dissolved in another solvent and subsequently, added the copolymer solution into the iron-curcumin complex containing organic phase.

The core-shell structure of the nanoparticles can then be achieved by mixing in an aqueous phase, which may comprise phosphate buffered saline (PBS) or an isotonic solution comprising, for example, 0.9% sodium chloride solution, 0.45% sodium chloride solution with 2.5% dextrose, 5% dextrose solution, or the like, with the iron-curcumin complex/copolymers containing organic mixture. Based on the solubility difference between the two phases, a self-assembly of the amphiphilic copolymers will be induced thereby forming the core-shell structures, i.e. each comprising an iron-curcumin complex core and an amphiphilic copolymer comprising shell. In one embodiment, the aqueous phase may comprise, for example, only water or deionized water.

Preferably, the method may further comprise a step of stabilizing the formed core-shell particles by at least one stabilizing agent such as a surfactant, as described above. More preferably, the surfactant is dissolved in an aqueous medium such as water, deionized water, isotonic solution or PBS prior to reacting or mixing with the formed core-shell particles to thereby stabilize the formed core-shell particles. In one embodiment, the surfactant can be priorly dissolved in the aqueous phase of the previously step, i.e. the core-shell structure forming step.

Figure 7:
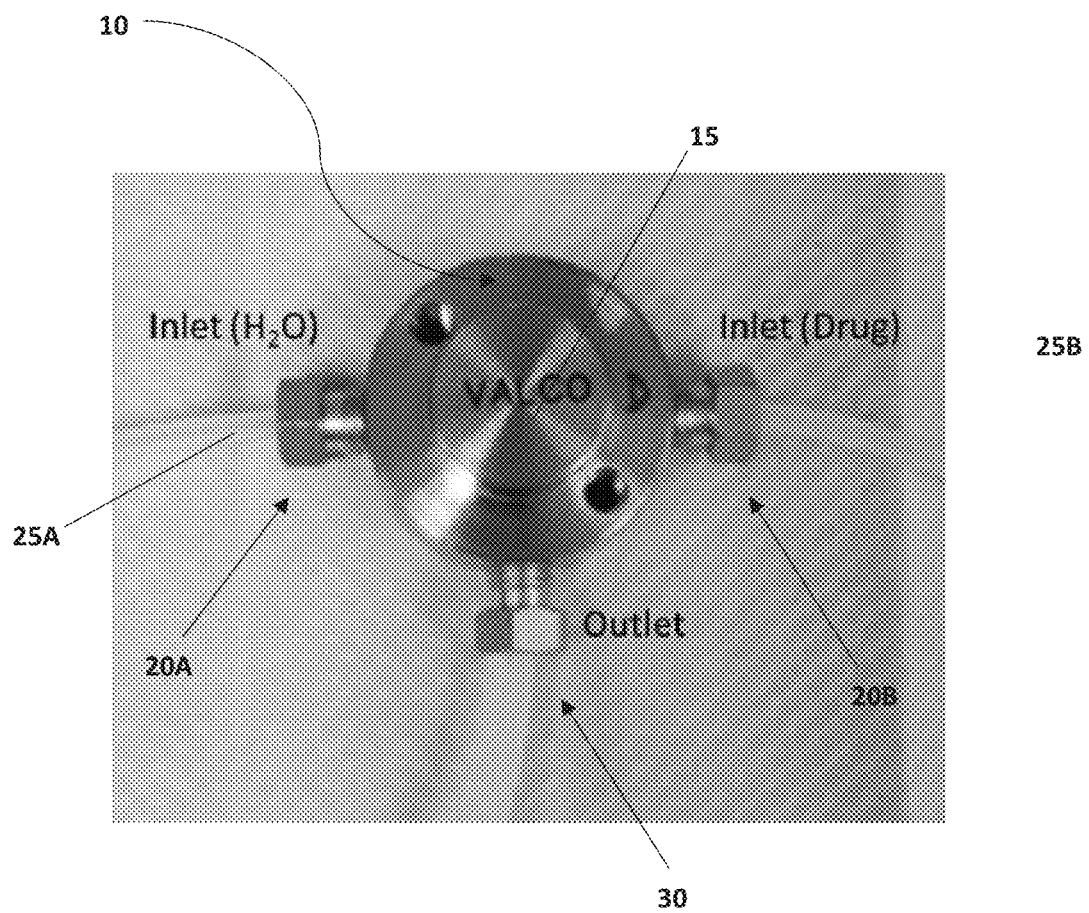
FIG. 7 shows an arrangement of the T-joint mixing device in accordance with an embodiment of the present invention.
Figure 8:
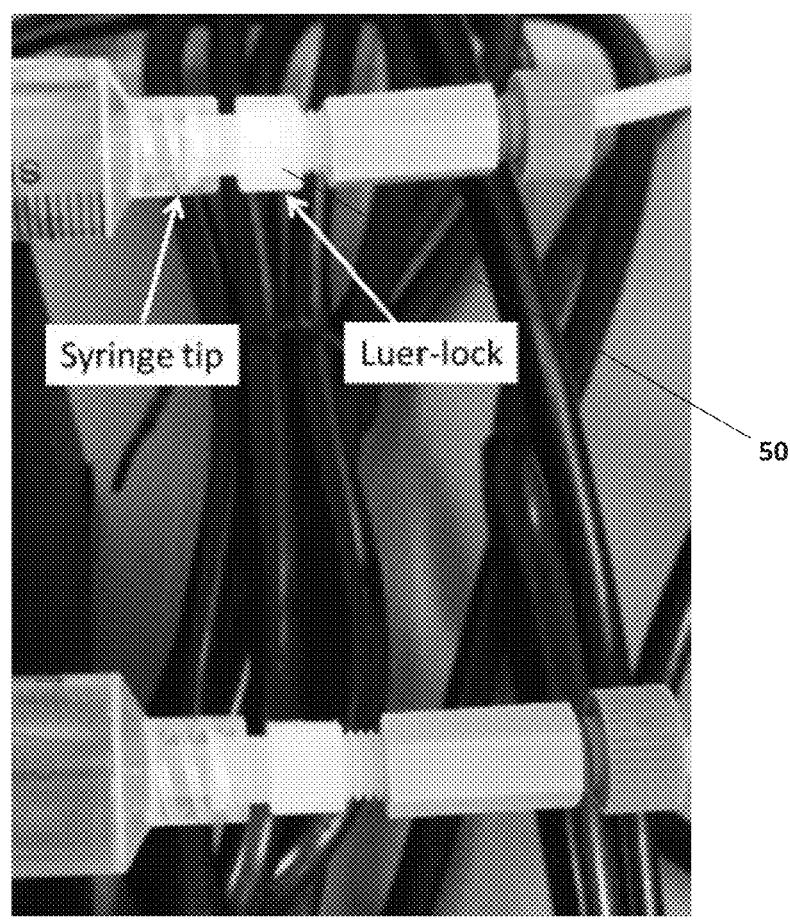
FIG. 8 shows the connections between the syringes and the injection tubes via the respective luer-locks according to an embodiment of the present invention.
Figure 9:
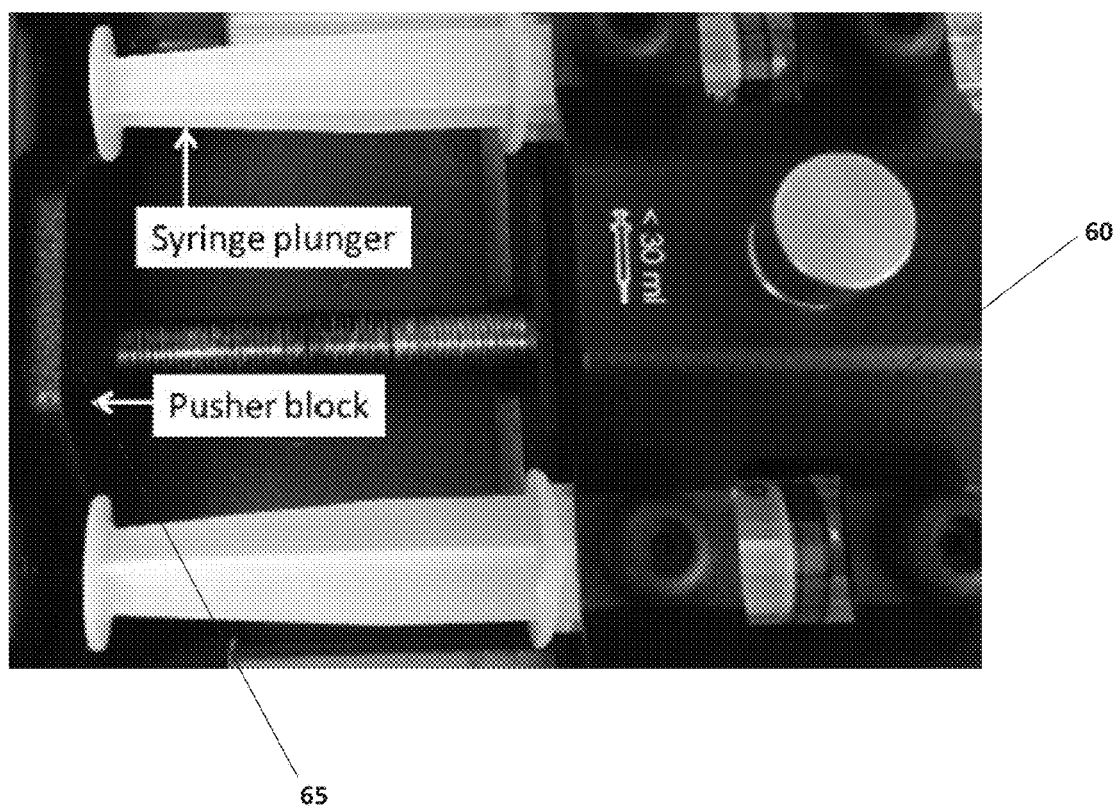
FIG. 9 shows an arrangement between the syringes and the syringe pump in accordance with an embodiment of the present invention.

In one further embodiment, the mixing between the aqueous phase with the iron-curcumin complex containing organic phase may be conducted via a mixing device 10 having at least two inlets 20A, 20B and at least one outlet 30, as shown in FIG. 7. The device 10 may comprise any commercially and/or industrially available adaptors or mixers, or can be any tailored or customized for the purpose of mixing two or more fluids. Preferably, the device 10 may comprise only two inlets 20A, 20B and one outlet 30, as shown in the figure, although alternative arrangements having more than two inlets and more than one outlet, shall also be encompassed depending on the specific needs and purposes of the mixing. More preferably, the mixing device 10 is configured to convey two inlet streams to concurrently impinge and mix in the device 10, such as in the form of a T-shape configuration, with the two, opposing inlets 20A, 20B arranged to direct the streams of organic mixture and the aqueous phase to substantially mix at the fluidly connected cavity 15 therebetween, and subsequently, allow the solution mixture to discharge via the at least one outlet 30. The device 10 may optionally be connected or equipped with one or more containers and/or conduits such as syringes and/or tubes to facilitate or to provide a better control of the mixing process. The containers and/or conduits may further be connected via one or more connectors or adaptors, such as one or more luer-locks as shown in FIG. 8, for example. The device 10 may also be connected or equipped with one or more instruments or apparatuses for controlling, adjusting and/or monitoring the flow rates of the fluids passing through the one or more inlets and outlet, see for example, the syringe pump as shown in FIG. 9.

For example, in one specific embodiment, the iron-curcumin complex containing organic mixture and the aqueous phase can be separately introduced via the two respective inlets 20A, 20B into the mixing device 10 to thereby form a solution mixture. Due to the solubility difference, the amphiphilic copolymers will self-assemble with the iron-curcumin complex to form nanoparticles with the core-shell structures, i.e. each having an iron-curcumin complex core and an amphiphilic copolymer comprising shell. The solution mixture will then be discharged via the outlet 30, with the solution mixture optionally collected in an aqueous medium comprising, for example, PVP dissolved in deionized water. The PVP aqueous solution is adapted to stabilize the formed core-shell structure, as well as to reduce a size of the formed core-shell particles.

Figure 10:
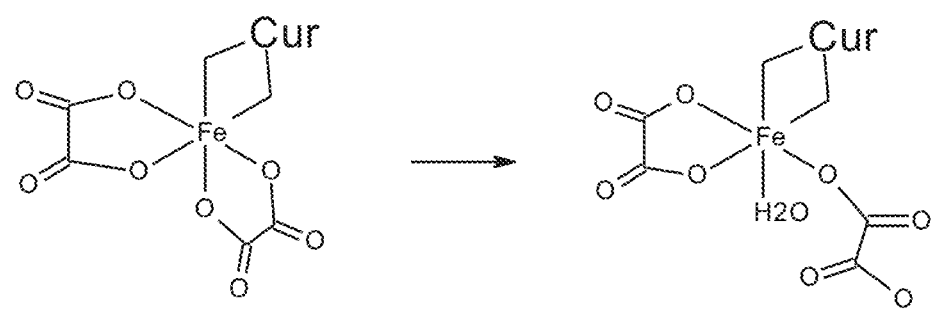
FIG. 10 shows a molecular scheme of an iron ion-curcumin-oxalate complex in accordance with a further embodiment of the present invention.
Figure 11:
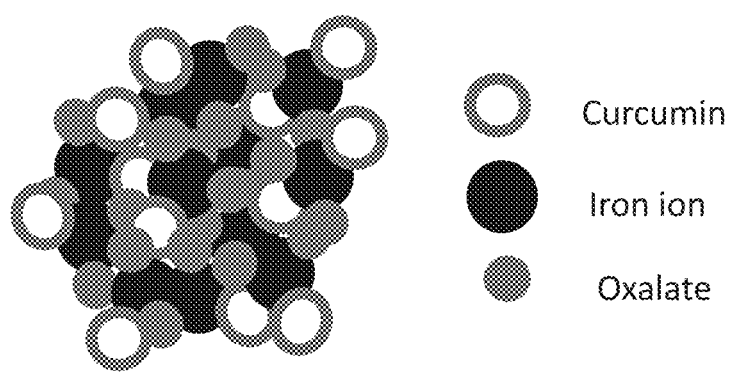
FIG. 11 is a schematic diagram showing the complex of FIG. 10.

Referring to FIGS. 10-11, shown is a further embodiment of the composition in accordance with the present invention. Particularly, the embodied composition comprises a metal ion containing compound having at least one metal ion adapted to bind with at least one first chelating agent, such as but not limited to, a curcumin molecule for targeting a region of interest such as but not limited to beta amyloid (Aβ) proteins; and at least one second chelating agent, such as but not limited to, an oxalate molecule which comprises at least one functional group capable of dissociating in an aqueous medium. The dissociation of the oxalate molecule allows or enhances contrast of the viewed region of interest under the medical imaging. As earlier described, the region of interest may comprise one or more proteins or protein molecules, and particularly, proteins or protein molecules relating to one or more neurodegenerative diseases or conditions such as, but not limited to, Alzheimer's disease (AD). In one embodiment, the protein or protein molecules comprises beta amyloid (Aβ) proteins and/or their aggregates in various forms.

Preferably, the first chelating agent may comprise one or more of a curcuminoid, a flavonoid, a resveratrol, a compound thereof, a derivative thereof and/or a mixture thereof; and the second chelating agent may comprise one or more of an oxalate, an oxalate derivative, a salt thereof and/or a mixture thereof. The metal ion may comprise one or more ferromagnetic metal ions, and preferably, iron metal, iron metal ion and/or iron metal atom as in the earlier embodiments.

In one embodiment, the metal ion, the first chelating agent and the second chelating agent are preferred to be in a mole ratio of about 1:1:2, respectively. More preferably, the composition may comprise a complex of iron ion, curcumin and oxalate in a mole ratio of about 1:1:2, respectively, with the oxalate ligands and the curcumin ligand being arranged and bound with one centrally located iron ion to thereby form a coordinate complex of $FeCurOx_2$, as shown in the chemical schemes of FIG. 10. The oxalate ligands of the complex is capable of dissociating slowly or a controlled manner in an aqueous medium, for example, after the composition being administered or injected into the blood stream of the subject. The dissociation of the oxalate ligands allow the coordinate structure of the complex to "open up", as shown in FIG. 10, so as to enable an exchange of one or more water molecules from the aqueous medium with one or more valence spaces of the central iron ion after the valence spaces are made available after the dissociation. The exposure of the central iron ion with water molecules is known to contribute to the improvement or enhancement of contrast signal of the tagged region of interest under the MRI.

Although oxalate has been exemplified as one specific chelating agent in the embodiments herein described, one skilled in the art will appreciate that the present invention should not be restricted to the specific examples provided, but any other chelating compounds or ligands which are adapted to complex with the central metal ion of the composition, and are capable of dissociating for a molecular exchange in an aqueous medium to thereby improve or enhance contrast signal or sensitivity under the MRI, shall also be encompassed, as long as they are considered suitable and applicable for the present invention without departing from the inventive concept.

Depending on the specific chemical structure, composition, as well as concentration of the complex in the metal ion containing compound, the formed complexes may appear as a random cluster due to various inter-molecular attractions possible such as ionic attraction, and the inter-molecular attractions may further enable the iron ion-curcumin-oxalate complex to grow in size thus forming one or more iron ion-curcumin-oxalate complex particles, as shown in FIG. 11. Alternatively, the iron ion-curcumin-oxalate complexes may be present in their free, molecular form, with no particulate as formed being detectable.

Figure 12:
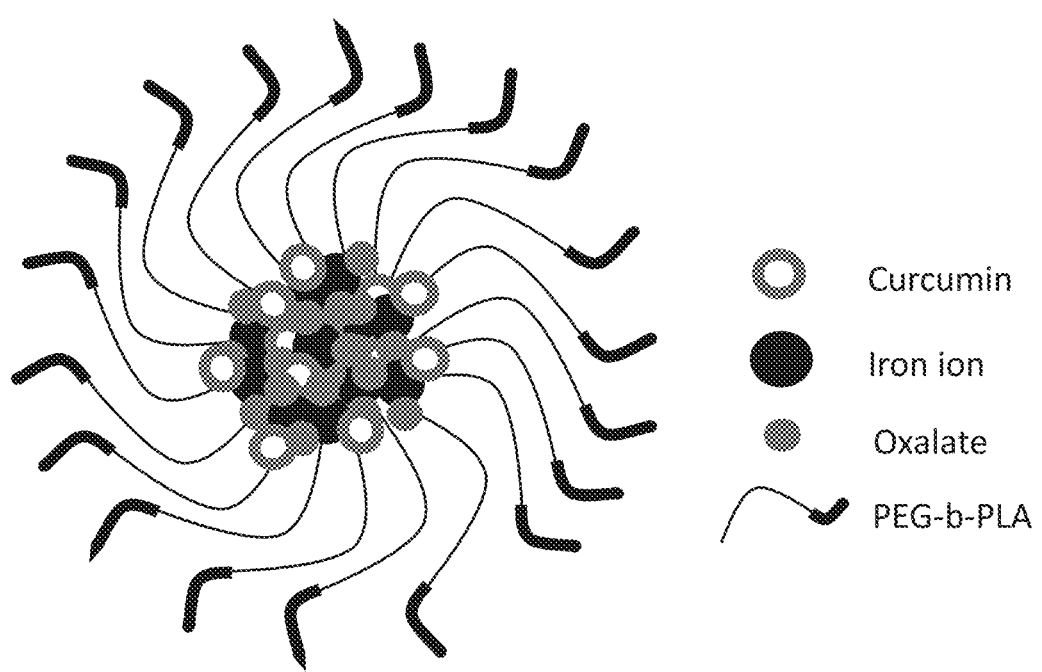
FIG. 12 is a schematic diagram showing a core-shell nanoparticle having an iron ion-curcumin-oxalate complex core and an amphiphilic PEG-b-PLA copolymer shell in accordance with an embodiment of the present invention.
Figure 13:
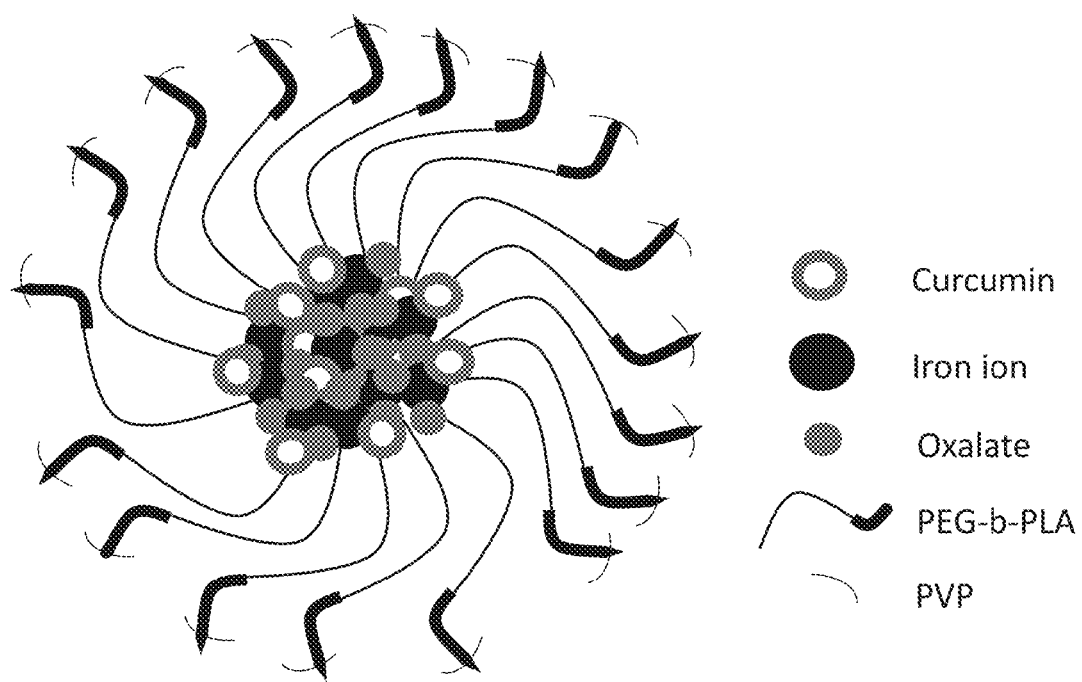
FIG. 13 is a schematic diagram showing the core-shell nanoparticle of FIG. 12 stabilized by PVP in accordance with an embodiment of the present invention.

In one further embodiment, the iron ion-curcumin-oxalate complex can be arranged to be surrounded by amphiphilic copolymers, and preferably, PEG-b-PLA copolymers, thereby forming nanoparticles with core-shell structures, i.e. each comprising an iron ion-curcumin-oxalate complex comprising core surrounded by an amphiphilic copolymers comprising shell, as shown in FIG. 12. Similar to the previous embodiments, the amphiphilic copolymer is preferred to comprise at least one hydrophilic block and at least one hydrophobic block, with the hydrophilic block being shorter than the hydrophobic block. The at least one hydrophobic block is arranged to adjacent the metal ion containing compound comprising core, and the at least one hydrophilic block is arranged to distal to and extended away from the metal ion containing compound comprising core. Various examples of the amphiphilic copolymers have been described in the earlier embodiments and therefore not to be repeated here. The core-shell nanoparticles may further be stabilized by using a stabilizing agent such as a surfactant, for example polyvinyl pyrrolidone (PVP), to form a stabilized core-shell structure, as shown in FIG. 13. Other examples of surfactants have also been discussed in the previous embodiments. In one specific embodiment, the stabilized core-shell particle having an iron ion-curcumin-oxalate complex comprising core and PEG-b-PLA copolymers comprising shell is of an average size equal to or smaller than about 100 nm in diameter, or more preferably, about 80 nm in diameter.

In another aspect, the present invention relates to a diagnostic agent for use in medical imaging such as, but is not limited to, MRI and that the diagnostic agent comprises the composition of any one of the embodiments as herein described. The present invention also relates to a diagnostic agent for use in amyloid (Aβ) protein detection under MRI, and that the diagnostic agent comprises the composition of any one of the embodiments as herein described.

In one further aspect, the present invention also relates to a method of preparing one or more of the above described embodiments of the composition. The method may comprise the steps of, for example, providing a metal ion-chelating agent complex such as an iron ion-curcumin-oxalate complex in an organic solution to form an organic phase; introducing an amphiphilic copolymer such as PEG-b-PLA copolymers to the organic phase to form an organic mixture; and subsequently, mixing an aqueous phase with the organic mixture thereby forming core-shell particles each having an iron ion-curcumin-oxalate complex comprising core and an amphiphilic copolymer comprising shell. The mixing between the aqueous phase with the iron-curcumin-oxalate complex/copolymer containing organic mixture can be conducted via the T-joint mixing device 10 as shown in FIG. 7, along with the relevant set up and supporting instruments or apparatus as shown in FIGS. 8 and 9. In one embodiment, the mixing steps of the organic mixture with the aqueous phase in forming the core-shell particles are substantially similar to the mixing procedure as described in the previous embodiments.

EXAMPLES

The following examples illustrate exemplified processes with steps for preparing one or more of the embodied compositions as described above.

Iron Ion-Curcumin Complex ($FeCur_3$) Nanoparticles
Preparation of the Iron-Curcumin Complex Particles 180 mg of iron nitrate ($Fe(NO_3)_3 \cdot 9H_2O$; 0.45 mmol) was weighed and dissolved in 5 mL of dimethylformamide (DMF). Separately, 500 mg of curcumin (1.36 mmol) was weighed and dissolved in 25 mL of DMF in a 200 mL round-bottom flask. Both of the solutions were sonicated until the iron nitrate and the curcumin were completed dissolved. The content of iron nitrate and curcumin are prepared in a 1:3 mole ratio.

The iron nitrate solution was then added dropwise to the curcumin solution, with color of the mixture slowly turning from deep orange to brown showing the formation of the complex. The round bottom flask was then wrapped with aluminum foil to ensure the reaction carried out under darkness, i.e. in the absence of light. The reaction was carried out at room temperature overnight.

After the overnight reaction, the reaction mixture was lyophilized and a viscous gel was obtained. 100 mL of deionized water was added to the flask and it was sonicated for 10 minutes for washing. Deep brown precipitate was observed during the sonication. The mixture was then transferred to 50 mL centrifuge tube and was centrifuged at 7800 rpm at 4° C. for 10 minutes. The supernatant was discarded and slurry precipitate was obtained. This washing process with centrifugation was repeated twice with deionized water to remove the nitrate salts.

About 10 mL of dichloromethane (DCM) was added to the slurry precipitate and the mixture was sonicated for 1-2 minutes. The mixture was then centrifuged and the supernatant was discarded. This washing process was repeated once to remove any unbound iron and/or curcumin. After the washing process, the powder was lyophilized by using a freeze dryer overnight. Deep brown powder of the iron-curcumin complex was obtained.

Preparation of the Core-Shell Nanoparticles with Iron-Curcumin Complex Cores and Amphiphilic Diblock Copolymer Shells Stabilized by PVP 40 mg of the prepared iron-curcumin complex powder was weighed and dissolved in 8 mL of DMF to obtain a solution at a concentration of 5 mg/mL. Subsequently, 80 mg of PEG(2k)-b-PLA(10k) diblock copolymer was weighed and transferred to the iron-curcumin complex/DMF solution. The content of the iron-curcumin complex powder and the PEG(2k)-b-PLA(10k) diblock copolymer were prepared in 1:2 mass ratio. The mixture was sonicated for 10 minutes to ensure the diblock copolymer was completely dissolved. The solution was then filtered by a 0.45 μm PTFE filter.

0.3% of polyvinylpyrrolidone-K30 (PVP-K30) solution was separately prepared by dissolving 0.3 g of PVP-K30 into 100 mL deionized water to form a PVP aqueous solution.

7 mL of the iron-curcumin complex/diblock copolymer/DMF solution and 7 mL of deionized water were separately prepared in two 10 mL syringes, respectively. The syringes were then connected to the T-joint mixing device 10 (as shown in FIG. 7) via the inlets 20A, 20B using injection tubes 25A, 25B. Specifically, the tips of the syringes were connected to the injection tubes 25A, 25B via the respective luer-locks 50, as shown in FIG. 8. The syringes were then loaded to a syringe pump 60, with the pusher blocks 65 engaging the plungers of the respective syringes, as shown in FIG. 9. The corresponding details of the syringes including one or more their dimensions, configurations, brands and models etc. were input to the control system of the syringe pump 60 as control parameters for the flow rate. In one embodiment, the syringe pump 60 can be controlled and/or adjusted to allow one or more specific flow rates at the respective inlets 20A, 20B ranged from about 10 mL/min to 60 mL/min, for example.

Core-shell nanoparticles having iron-curcumin complex cores and diblock copolymer shells were prepared through T-joint mixing device 10 under a pump flow rate of 35 mL/min. The initial 5 mL of the liquid mixture, i.e. 2.5 mL from each of the syringes, was discarded. Then the subsequent 5 mL of the liquid mixture comprising the core-shell nanoparticles was collected with a container with 45 mL of 0.3% PVP-K30 solution. The resulting solution was stirred at 400 rpm to form the PVP stabilized core-shell nanoparticles. Clear orange solution was obtained and the formed nanoparticles were characterized by a particle size analyzer.

The mixture having the formed PVP stabilized core-shell nanoparticles was purified by dialysis (Spectra/Por 1 Dialysis Tubing, 6-8 kD MWCO) against deionized water, stirred at 300 rpm at 4° C., to thereby remove the residual DMF in the solution. The deionized water was changed every hour for the first 3 hours and then the dialysis was continued overnight. The purified core-shell nanoparticles were then collected and stored at 4° C.

Characterization of the Synthesized Core-Shell Nanoparticles

The synthesized core-shell nanoparticles particles were characterized by nanoparticle size and zeta potential analyzer (Malvern Zetasizer Nano-ZS90), with the measured particle sizes and polydispersity indexes (PDI) for three separate batches of nanoparticles synthesized under the same formulation and condition being shown in Tables 1 and 2 below. The characterization revealed a mean particle size of 55.34 nm, with a narrow mean PDI of 0.178 for the three batches of the core-shell nanoparticles. The relatively low standard deviations (SD) and % relative standard deviations (% RSD) also support the high reproducibility of the nanoparticles achievable by the preparation method of the present invention.

TABLE 1

Particle sizes and polydispersity indexes (PDIs) of core-shell nanoparticles synthesized in three separate batches under the same condition.

| Batch No. | Size [nm] Before Dialysis | Size [nm] After Dialysis | PDI Before Dialysis | PDI After Dialysis |
|---|---|---|---|---|
| #1 | 63.94 | 59.71 | 0.156 | 0.181 |
| #2 | 60.40 | 50.18 | 0.205 | 0.188 |
| #3 | 65.42 | 56.12 | 0.184 | 0.165 |

TABLE 2

Standard deviations (SD) and % relative standard deviations (% RSD) for the measured particles sizes and PDIs of Table 1.

| | Mean | SD | % RSD |
|---|---|---|---|
| Size After Dialysis | 55.34 | 4.81 | 8.70 |
| PDI After Dialysis | 0.178 | 0.012 | 6.620 |

Magnetic Resonance Imaging (MRI) of Amyloid Proteins Targeting by the Synthesized Core-Shell Nanoparticles with Iron-Curcumin Complex Cores and Amphiphilic Diblock Copolymer Shells Stabilized by PVP The synthesized, PVP stabilized core-shell nanoparticles having iron-curcumin complex cores and amphiphilic diblock copolymer shells were tested in AD diseased mice for their potential targeting of beta amyloid (Aβ) protein aggregates in brain tissues under the MRI. Specifically, core-shell nanoparticles (400 μl of nanoparticle suspension which contains 3.75 mg Fe/ml) prepared in accordance with the above described methods, were administered via intravenous (IV) injection into an AD diseased mouse. The brain of the mouse was scanned in vivo under a 2-D FLASH MRI 4 hours after the injection. A healthy, non-AD diseased mouse was also injected with the core-shell nanoparticles prepared under the same condition, and was scanned under the same MRI setting as a control experiment. Both the AD diseased mouse and the healthy, control mouse are of about 7 months old. Both mice were anesthetized (5 ml/kg body weight) with a mixture of 100 mg/ml ketamine and 10 mg/ml xylazine in phosphate-buffered saline (PBS). For each of the mice, skin of the left leg was cut open to expose the femoral vein. Injection of the nanoparticle suspension to the mice was done using the smallest gauge needle (G30), and the injection area was magnified using a magnifying glass. After the injection, the cut in the left leg of each of the mice was sewn up, and the mice were kept for 4 hours prior to the MRI scan. During the MRI scan, the mice were anesthetized by inhalation of isoflurane mixed with air, and their body temperatures were kept at 37° C. by temperature-controlled water blanket. Both mice were scanned by 7-tesla MRI, with the parameter settings as shown in Table 3 as follows:

TABLE 3

Parameter settings for MRI scanning.

*2D-FLASH,
TE/TR = 12.8/1000 ms
5 averages
42 min 40 sec scan time
Flip angle 60 degrees
RF pulse sinc 3, 1.8 ms duration
Effective spectral bandwidth 25 kHz
Short TE optimization
25.6 mm × 25.6 mm FOV
512 × 512 matrix
0.3 mm slice thickness
15 slices
Motion suppression on MRI Results and Analysis Serial MRI images produced from whole brain scans on the AD diseased mouse and the control mouse are shown in FIG. 10. Specifically, column A, i.e. the left column of FIG. 10, shows the MRI images of the AD diseased mouse being scanned from a rear position (#1) to a frontal position (#15) of the brain progressively; and column B, i.e. the right column of FIG. 10, shows the MRI images of the non-AD diseased mouse being scanned from a corresponding rear position (#1) to a corresponding frontal position (#15) of the brain.

The full brain scan of the AD diseased mouse revealed a number of dark spots in various sizes, shapes and darkness and are consistently visible in every one of the MRI images from positions #1 to #15. No dark spots are seemed to be present in the MRI images from the corresponding scans of the healthy, non-AD diseased mouse. The dark spots are believed to be caused by the accumulation or localization of the core-shell iron-curcumin complex nanoparticles of the present invention, which indicate the presence of beta amyloid (Aβ) proteins or aggregates of such proteins under the MRI due to the strong affinity of the nanoparticles with beta amyloid (Aβ) proteins. In other words, the beta amyloid (Aβ) protein aggregates in the brain tissues of the AD diseased mouse are found to be successfully taggable by the core-shell iron-curcumin complex nanoparticles, with the iron-curcumin complex core of the nanoparticles being visualisable or identifiable under the MRI due to the magnetizability of the iron-curcumin complex.

The nanoparticles of the present invention thus serve as a useful means to indicate the presence of and/or to provide location information of amyloid (Aβ) protein aggregates under the MRI, with potential applications in the detecting or diagnosing of Alzheimer's disease in animal and human subjects, as well as to allow, improve or enhance visibility and/or contrast of the detected amyloid (Aβ) aggregates under the MRI. The sufficiently small size of the core-shell nanoparticles, with the core having a diameter of less than 10 nm in general, further enable their binding not only to the relatively large targets of the beta amyloid (Aβ) plaques in the brain tissues, but also beta amyloid (Aβ) fibrils and/or oligomers. It is known that beta amyloid (Aβ) fibrils and/or oligomers are typically too small to be effectively traceable and/or taggable by any traditional techniques, and therefore the ability for the present invention to identify or detect the presence of these beta amyloid (Aβ) fibrils and oligomers represent a significant improvement to the diagnosis and treatment of protein relating neurodegenerative diseases such as, but not limited to, Alzheimer's disease (AD) at early stage. In addition, the nanoparticles of the present invention are found to be capable of effectively penetrating the blood brain barrier, as well as targeting the amyloid aggregates in brain tissues with shorter scanning and imaging time (i.e. of about 40 minutes) under the MRI. This is in contrast to, and thus demonstrates an improvement to, the traditional MRI methods which may usually require over 60 minutes of scanning and imaging in order to produce the same quality of images. The present invention thus offers higher sensitivity when compared with the traditional MRI methods.

Iron Ion-Curcumin-Oxalate Complex (FeCurOx$_2$) Nanoparticles

Preparation of the Iron Ion-Curcumin-Oxalate Complex (FeCurOx$_2$) Stock Solution 400 mg of iron nitrate (Fe(NO$_3$)$_3$.9H$_2$O) was dissolved in 10 mL of dimethylformamide (DMF) followed by the addition of 187 mg of oxalic acid. The mixture was stirred for 1 hour. 364 mg of curcumin was weighed and dissolved in 1 mL of DMF. The curcumin solution was then added dropwise into the iron nitrate/oxalic acid solution. The reaction was then stirred overnight in darkness under ambient temperature.

Preparation of the Core-Shell Nanoparticles with Iron Ion-Curcumin-Oxalate Complex Cores and Amphiphilic Diblock Copolymer Shells Stabilized by PVP A 5 mg/mL FeCurOx$_2$ solution was prepared by diluting 0.65 mL of the prepared FeCurOx2 stock solution using 4.35 mL DMF. 70 mg of PEG(2k)-b-PLA(10k) di-block copolymer was weighed and dissolved in 2 mL of DMF. The di-block copolymer solution was then filtered by using a 0.45 μm PTFE filter, and the filtrate was added to the FeCurOx$_2$ solution.

The core-shell nanoparticles formation was performed by using the T-joint mixing device as described above. Two 10 mL-syringes were separately filled up with an equal amount (e.g. 6 mL) of FeCurOx$_2$ solution and deionized water. A beaker carrying 45 mL of polyvinylpyrrolidone-K30 (PVP-K30, 0.3% w/v) solution was used to collect the nanoparticles-comprising solution mixture at the outlet of the T-joint device. The syringe pump was set at a flow rate of 35 min/mL and a volume of 2.5 mL. The resulting PVP stabilized nanoparticles solution (50 mL) was then dialyzed with a dialysis bag (6k-8k) with deionized water at 4° C., with replacement by fresh deionized water every hour for the first 3 hours and then dialysis overnight.

Determination of Relaxivities of the Synthesized Core-Shell Nanoparticles

During an MRI study, an MRI contrast agent generally shortens the value of a characteristic time constant known as the relaxation time of the nearby water protons at the tissues being examined to thereby enhance contrast of the image. The relaxivity of a contrast agent reflects how the relaxation rates of a solution change as a function of concentration [C]. Since a contrast agent may individually affect two relaxation rates (1/ΔT1 and 1/ΔT2), the degree of contrast as provided by a contrast agent is generally characterized under two corresponding relaxivities, i.e. r1 and r2 (L/mmol-s), which are defined by:

$$1/\Delta T1 = r1 \cdot [C]$$

and $$1/\Delta T2 = r2 \cdot [C]$$

The relaxation rates of a contrast agent in solution are obtained by graphing changes in relaxation rates (1/ΔT1) and (1/ΔT2) at different concentrations, with r1 and r2 being determined by the slopes of the graph.

Magnetization tests were conducted using the synthesized iron ion-curcumin-oxalate complex (FeCurOx$_2$) core-shell nanoparticles and iron ion-curcumin complex (FeCur$_3$) core-shell nanoparticles, along with iron nitrate (Fe(NO$_3$)$_3$) and a commercially available, clinically used gadolinium contrast agent (GdCl3) as control experiments. For each of the contrast agents being tested, samples have been prepared in 10 different concentrations, namely, 1000 µg/ml, 750 µg/ml, 500 µg/ml, 250 µg/ml, 125 µg/ml, 62.50 µg/ml, 31.25 µg/ml, 15.63 µg/ml, 7.81 µg/ml and 3.91 µg/ml using DMF:H$_2$O 4:1 as solvent for dilution of the respective stock samples.

Table 4 below shows the results of the determined relaxivities r1 and r2 of the tested contrast agents under the MRI. It is revealed that the iron ion-curcumin-oxalate complex (FeCurOx$_2$) core-shell nanoparticles prepared in accordance with the present invention have demonstrated a molecular weight adjusted r1 (L/mmol-s) of more than double to that of the commercially available gadolinium contrast agent (GdCl$_3$), and a molecular weight adjusted r2 (L/mmol-s) of almost 3 times to that of the commercially available gadolinium contrast agent (GdCl$_3$). In addition, the iron ion-curcumin complex (FeCur$_3$) core-shell nanoparticles prepared in accordance with the present invention also demonstrated a higher r2 (L/mmol-s) than that of the commercially available gadolinium contrast agent (GdCl$_3$).

TABLE 4

Relaxivities r1 and r2 of the tested contrast agents under MRI.

| Relaxivities | Fe(NO$_3$)$_3$ (1/s) | GdCl$_3$ (1/s) | FeCur$_3$ (1/s) | FeCurOx$_2$ (1/s) |
|---|---|---|---|---|
| r1 (mL/µg-s) | 0.0004 | 0.0494 | 0.0238 | 0.0491 |
| r2 (mL/µg-s) | 0.064 | 0.0567 | 0.046 | 0.0708 |
| MW (g/mol) | 242 | 264 | 424 | 600 |
| r1 (L/mmol-s) | 0.0968 | 13.0416 | 10.0912 | 29.46 |
| r2 (L/mmol-s) | 15.488 | 14.9688 | 19.504 | 42.48 |

It is therefore demonstrated that the composition of the present invention can serve as a potent contrast agent for use in medical imaging such as MRI which enables a significantly improved or enhanced contrast of the examined target of interest. The improvement in the contrast and thus sensitivity of the MRI relates to the dissociation of the oxalate ligands, which allows the coordinate structure of the complex to "open up", enabling an efficient water exchange of the central iron ion with the aqueous medium. Particularly, for the iron and curcumin-comprising complex as being generally hydrophobic in nature, the dissociation of the oxalate molecule further increases chances for the central iron ion as being exposed to the surrounding water to thereby further enhance the contrast signal. It has also been proven by the previously embodiments that the curcumin comprising complex nanoparticles are capable of binding with beta amyloid (Aβ) proteins. The present invention is thus advantageous in detecting the presence of and/or to provide location information of amyloid (Aβ) protein aggregates under the MRI at increased contrast, with potential applications in the diagnosing of Alzheimer's disease in animal and human subjects. Also as earlier described, the sufficiently small size of the core-shell nanoparticles further enable their binding not only to the relatively large targets of the beta amyloid (Aβ) plaques in the brain tissues, but also beta amyloid (Aβ) fibrils and/or oligomers which allows the diagnosis and treatment of protein relating neurodegenerative diseases such as Alzheimer's disease (AD) at early stage. Last but not least, the composition of the present invention demonstrates much lower toxicity than the conventional contrast agents such as gadolinium-based contrast agents, which are commonly used in clinical tests and MRI studies. In contrast to gadolinium metal which is known to affect kidney functions, any presence of iron in the blood stream will eventually be absorbed by the subject as iron reserve. Oxalate and curcumin are also known to be biodegradable and/or biocompatible for pharmaceutical purposes.

The present description illustrates the principles of the present invention. It will thus be appreciated that those skilled in the art will be able to devise various arrangements that, although not explicitly described or shown herein, embody the principles of the invention and are included within its spirit and scope.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

While the invention has been illustrated and described in detail in the drawings and foregoing description, the same is to be considered as illustrative and not restrictive in character, it being understood that only exemplary embodiments have been shown and described and do not limit the scope of the invention in any manner. It can be appreciated that any of the features described herein may be used with any embodiment. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

In the claims hereof, any element expressed as a means for performing a specified function is intended to encompass any way of performing that function. The invention as defined by such claims resides in the fact that the functionalities provided by the various recited means are combined and brought together in the manner which the claims call for. It is thus regarded that any means that can provide those functionalities are equivalent to those shown herein.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art.

The invention claimed is:

1. A composition for use as a contrast agent in Magnetic Resonance Imaging (MRI) the composition comprising: at least one iron metal ion, said at least one iron metal ion being magnetisable and bound to metal ion chelating agents to form a metal ion containing compound; wherein said metal ion containing compound is surrounded by amphiphilic copolymers, and is releasable from the amphiphilic copolymers; wherein said metal ion chelating agents comprise at least one curcumin comprising first chelating agent and at least one oxalate comprising second chelating agent, such that when the metal ion containing compound is released from the amphiphilic copolymers, the at least one curcumin-comprising first chelating agent of the metal ion containing compound is adapted to target a region of interest being imaged by binding to one or more proteins of said region of interest, and the at least one oxalate-comprising second chelating agent of the metal ion containing compound is adapted to dissociate in an aqueous medium to thereby allow or enhance contrast of the region of interest under MRI.

2. The composition according to claim 1, wherein the curcumin comprising first chelating agent comprises at least one functional group that binds with one or more proteins.

3. The composition according to claim 2, wherein the one or more proteins comprise beta amyloid (Aβ) proteins.

4. The composition according to claim 1, wherein the iron metal ion, the curcumin-comprising first chelating agent and the oxalate-comprising second chelating agent of the metal ion containing compound are in a mole ratio of about 1:1:2, respectively.

5. The composition according to claim 4, wherein the iron metal ion comprises a centrally located iron ion, such that the oxalate of the second chelating agent and the curcumin of the first chelating agent complex with the centrally located iron ion to form a coordinate complex.

6. The composition according to claim 1, wherein at least one functional group of said at least one oxalate comprising second chelating agent dissociates and exchanges with water in the aqueous medium.

7. The composition according to claim 1, where the amphiphilic copolymers surround the metal ion containing compound thereby forming particles of core-shell structures, with each of the core-shell structure comprising a metal ion containing compound comprising core and an amphiphilic copolymer comprising shell.

8. The composition according to claim 7, wherein each of the core-shell structures is of an average size of smaller than or equals to about 100 nm in diameter.

9. The composition according to claim 7, wherein the amphiphilic copolymers each comprises at least one hydrophilic block and at least one hydrophobic block, with the hydrophilic block being shorter than the hydrophobic block.

10. The composition according to claim 9, wherein the at least one hydrophobic block is arranged to adjacent the metal ion containing compound comprising core, and the at least one hydrophilic block is arranged to distal to and extended away from the metal ion containing compound comprising core.

11. The composition according to claim 7, wherein the amphiphilic copolymers are selected from a group consisting of polyethylene glycol (PEG)-b-polylactic acid (PLA), polyethylene glycol (PEG)-b-polycaprolactone (PCL), polyethylene glycol (PEG)-b-polylactic-co-glycolic acid (PLGA), pethoxypolyethylene glycol (MePEG)-b-polylactic acid (PLA), pethoxypolyethylene glycol (MePEG)-b-polycaprolactone (PCL), pethoxypolyethylene glycol (MePEG)-b-polylactic-co-glycolic acid (PLGA), polyethylene oxide (PEO)-b-polybutadiene (PBD), and a mixture thereof.

12. The composition according to claim 7, further comprising a surfactant for stabilizing the core-shell structures.

13. The composition according to claim 12, wherein the surfactant is selected from a group consisting of polyvinyl pyrrolidone (PVP), polyvinyl alcohol (PVA), polyethylene glycols (PEG), hydroxypropyl methylcellulose (HPMC), poloxamers, polylactic-co-glycolic acid (PLGA), poly caprolactone (PCL), polylactic acid (PLA), poly(butyl)cyanoacrylate (PBCA), chitosan and a mixture thereof.

14. A diagnostic agent for use in amyloid (Aβ) protein detection under magnetic resonance imaging (MRI), comprising the composition according to claim 1.

15. A method of preparing a particle composition for use in medical imaging of claim 1, comprising the steps of: providing a metal ion-chelating agent complex of claim 1 in an organic solution to form an organic phase; introducing an amphiphilic copolymer to the organic phase to form an organic mixture; and mixing an aqueous phase with the organic mixture thereby forming core-shell particles each having a metal ion-chelating agent complex comprising core and an amphiphilic copolymer comprising shell.

16. The method according to claim 15, wherein the step of providing a metal ion-chelating agent complex comprises:
providing a metal compound comprising at least one metal ion;
dissolving the metal compound in an organic solvent; and
introducing a first metal ion chelating agent precursor and a second metal ion chelating agent precursor into the organic solvent to form the organic phase.

17. The method according to claim 15, wherein the step of providing a metal ion-chelating agent complex comprises binding of a metal ion with one or more metal ion chelating agents to form a metal ion-chelating agent complex.

18. The method according to claim 17, wherein the metal ion-chelating agent complex comprises at least one metal ion, at least one first metal ion chelating agent and at least one second metal ion chelating agent in a mole ratio of about 1:1:2, respectively.

19. The method according to claim 18, wherein the metal ion comprises at least one iron ion, the first metal ion chelating agent comprises curcumin, and the second metal ion chelating agent comprises oxalate.

20. The method according to claim 15, wherein the aqueous phase comprises phosphate buffered saline (PBS).

21. The method according to claim 15, wherein the mixing step comprises use of a mixing device having at least two inlets and at least one outlet, the mixing step comprising:
introducing the organic mixture and the aqueous phase separately via the at least two inlets into the mixing device thereby forming a solution mixture comprising the core-shell particles; and
discharging the solution mixture from the mixing device via the at least one outlet.

22. The method according to claim 21, wherein the mixing device is configured such that the at least two, opposing inlets are arranged to respectively direct the mixture and the aqueous phase to concurrently impinge and mix therebetween, and subsequently allow the solution mixture to discharge from the mixing device via the at least one outlet.

23. The method according to claim 15, further comprising a step of stabilizing the formed core-shell particles by at least one surfactant.

24. The method according to claim 23, wherein the at least one surfactant is dissolved in an aqueous medium prior to reacting with the formed core-shell particles to thereby stabilize the formed core-shell particles.

* * * * *